(12) United States Patent
Hill (10) Patent No.: US 8,673,375 B2
(45) Date of Patent: Mar. 18, 2014

(54) HERBAL EXTRACT PRODUCTS AND METHODS

(75) Inventor: Jacqueline Hill, Puidoux (CH)

(73) Assignee: Prime Interaction Holdings Limited, Triesen (LI)

( * ) Notice: Subject to any disclaimer, the term of this patent is extended or adjusted under 35 U.S.C. 154(b) by 331 days.

(21) Appl. No.: 12/937,140

(22) PCT Filed: Apr. 8, 2009

(86) PCT No.: PCT/GB2009/000920
§ 371 (c)(1),
(2), (4) Date: Apr. 12, 2011

(87) PCT Pub. No.: WO2009/125182
PCT Pub. Date: Oct. 15, 2009

(65) Prior Publication Data
US 2011/0206789 A1    Aug. 25, 2011

(30) Foreign Application Priority Data
Apr. 10, 2008  (GB) .................................. 0806543.5

(51) Int. Cl.
*A61K 36/58*  (2006.01)
*A61K 36/886*  (2006.01)

(52) U.S. Cl.
USPC ........... 424/744; 424/725; 424/761; 424/774; 424/773

(58) Field of Classification Search
None
See application file for complete search history.

(56) References Cited

U.S. PATENT DOCUMENTS

| | | | |
|---|---|---|---|
| 2004/0033273 A1 * | 2/2004 | Patwardhan et al. | ......... 424/725 |
| 2004/0156920 A1 | 8/2004 | Kane | |
| 2006/0004071 A1 * | 1/2006 | Bhatia et al. | .................. 514/389 |
| 2006/0105005 A1 | 5/2006 | Marenik et al. | |
| 2007/0098647 A1 * | 5/2007 | Neubourg | ........................ 424/47 |
| 2007/0196318 A1 * | 8/2007 | Marini | ............................ 424/74 |
| 2008/0081071 A1 | 4/2008 | Sanghvi et al. | |

FOREIGN PATENT DOCUMENTS

| | | |
|---|---|---|
| DE | 10140538 A1 * | 3/2003 |
| GB | 2353706 | 3/2001 |
| GB | 2 441 599 A * | 3/2008 |
| WO | WO 2006/008761 A2 | 1/2006 |
| WO | WO 2006/089348 A1 * | 8/2006 |
| WO | WO 2006/134409 A2 | 12/2006 |
| WO | WO 2006/134409 A3 | 12/2006 |
| WO | WO 2008/015698 A2 * | 2/2008 |

OTHER PUBLICATIONS http://www.diffen.com/difference/Eczema_vs_Psoriasis—accessed Feb. 2013.*
Laxmikant Sharma et al., "Medicinal plants for skin and hair care," Indian Journal of Traditional Knowledge, Resources, New Delhi, New Delhi—India, vol. 2, No. 1, Jan. 1, 2003, pp. 62-68, XP018021275 ISSN: 0972-5938.
R. Govindarajan et al., "Antioxidant approach to disease management and the role of 'Rasayana' herbs of Ayurveda," Journal of Ethnopharmacology 99, 2005, pp. 165-178.
V.K. Gupta, "Key Attributes of TKLD," RS1/730, pp. 4-26 (original Sanskrit and unofficial translation), 2000.
International Search Report, PCTGB2009/000920, Aug. 26, 2009, 5 pages.
Kandasamy Mudaliar; *Athmarakshaamirtham*, Pub: Ilakkana Achagam, Chennai (1879).
"Abu Bakr Mohammad.Bin Zakariyya Al-Razi," *Kitaab-al-Haawi-fil-Tibb*, vol. XX ($9^{th}$ Century AD) Dayerah-al Ma'aarif Usmania, Hyderabad, (First Edition), 1967.
"Pandita Narahari," *Rajanighantaub—Edited with Hindi Commentary by Indradeo Tripath*; Krishnadas Academy, Varanasi, Edn. $2^{nd}$, 1998.
"Suśruta," *Suśruta Samhita*—Edited & translated by P.V. Sharma, vol. II; Chaukhamba Visvabharati, Varanasi, Edn. $1^{st}$, 2000 (Time of origin 1000 BC $5^{th}$ Century).
Agniveśa, *Caraka Samhita*—Edited & translated by P.V. Sharma, vol. II, Chaukhamba Orientalia, Varanasi, Edn. $5^{th}$ 2000 (Time of origin 1000 BC , $4^{th}$ Century).
J.K. Latta et al., "Clinical trials of ayurvedic formulations in the treatment of acne vulgaris," *Journal of Ethnopharmacology*, 78, 2001, pp. 99-102.
Govinda Dasa, *Bhaisajya Ratnavali*—Edited by Rajeshvaradutta Shastri, translated by Ambikaduttashastri, Chaukhamba Sanskrit Sansthan, Varanasi, Edn. $14^{th}$, 2001. (This book contains back references from 1000 B.C. to $18^{th}$ Century).
Third Party Submission List of Publications submitted (Oct. 13, 2013).

* cited by examiner

*Primary Examiner* — Susan Hoffman
(74) *Attorney, Agent, or Firm* — Haynes and Boone, LLP (57) ABSTRACT

The present invention relates to a product for topical administration in particular, a product for use in the treatment of eczema and psoriasis and other related conditions.

20 Claims, 12 Drawing Sheets

Binomial Test

| | | Category | N | Observed Prop. | Test Prop. | Exact Sig. (2-tailed) |
|---|---|---|---|---|---|---|
| Reduction in redness | Group 1 | 0 | 5 | .26 | .50 | .064 |
| | Group 2 | 1 | 14 | .74 | | |
| | Total | | 19 | 1.00 | | |

Binomial Test

| | | Category | N | Observed Prop. | Test Prop. | Exact Sig. (2-tailed) |
|---|---|---|---|---|---|---|
| Reduction in discomfort | Group 1 | 0 | 5 | .26 | .50 | .064 |
| | Group 2 | 1 | 14 | .74 | | |
| | Total | | 19 | 1.00 | | |

Binomial Test

| Reduction in Itchiness | | Category | N | Observed Prop. | Test Prop. | Exact Sig. (2-tailed) |
|---|---|---|---|---|---|---|
| | Group 1 | 0 | 5 | .26 | .50 | .064 |
| | Group 2 | 1 | 14 | .74 | | |
| | Total | | 19 | 1.00 | | |

Binomial Test

| Reduction in bleeding | | Category | N | Observed Prop. | Test Prop. | Exact Sig. (2-tailed) |
|---|---|---|---|---|---|---|
| | Group 1 | 0 | 5 | .26 | .50 | .064 |
| | Group 2 | 1 | 14 | .74 | | |
| | Total | | 19 | 1.00 | | |

Binomial Test

| | | Category | N | Observed Prop. | Test Prop. | Exact Sig. (2-tailed) |
|---|---|---|---|---|---|---|
| Healthiness of skin | Group 1 | 2 | 6 | .32 | .50 | .187 |
| | Group 2 | 1 | 13 | .68 | | |
| | Total | | 19 | 1.00 | | |

Binomial Test

| | | Category | N | Observed Prop. | Test Prop. | Exact Sig. (2-tailed) |
|---|---|---|---|---|---|---|
| Overall rating | Group 1 | 0 | 4 | .21 | .50 | .019 |
| | Group 2 | 1 | 15 | .79 | | |
| | Total | | 19 | 1.00 | | |

HERBAL EXTRACT PRODUCTS AND METHODS

CROSS-REFERENCE TO RELATED APPLICATION

This is a national stage of PCT/GB2009/000920, filed Apr. 8, 2009, the contents of which is hereby incorporated herein in its entirety by express reference thereto.

The present invention relates to a product for topical administration, preferably in the form of a cream, lotion or ointment. In particular, the present invention relates to a product for topical administration for use in the treatment of eczema and psoriasis and other related skin conditions.

Eczema, or dermatitis as it is sometimes called, is a group of skin conditions which can affect all age groups.

In the United Kingdom, up to a ⅕ of all children of school age have eczema, along with about a 1/12 of the adult population. The severity of the disease, eczema, can vary. In mild forms, the skin is dry, hot and itchy, whilst in more severe forms, the skin can become broken and raw, and can actually result in bleeding.

The underlying causes behind eczema are many and varied and are dependent on the type of eczema a person has.

Atopic eczema is thought to be a hereditary condition. To this end, it is postulated that people with atopic eczema are sensitive to allergens in the environment, which are harmless to others. In atopic eczema, the body's immune system on coming into contact with an allergen overreacts. This results in inflamed, irritated and sore skin. Associated atopic conditions include asthma and hay fever.

Another form of eczema, known as allergic contact dermatitis, is caused by irritants such as chemicals and detergents and allergens such as nickel. As with atopic eczema, the body's immune system overreacts on coming into contact with an allergen. The resulting allergic reaction often develops over a period of time, that is, through repeated contact with the substance giving rise to eczema.

Other forms of eczema include infantile seborrhoeic eczema, adult seborrhoeic eczema, varicose eczema and discoid eczema.

Although there is currently no known cure for eczema, a number of treatments have been devised with a view to minimising the discomfort and distress associated with eczema.

There are a number of ways to manage eczema, all of which begin with an effective skin care routine. The most commonly used treatments include the use of:

Emollients

Emollients are necessary to reduce water loss from the skin, preventing the dryness normally associated with eczema. By providing a seal or barrier, the skin is less dry, itchy and more comfortable.

Emollients are available in various forms, including ointments for very dry skin, and creams and lotions for moderate forms of eczema. Some forms of emollients are directly applied to the skin, whilst other forms are used as soap substitutes or can be added to the bath.

One of the problems associated with some emollients already on the market is that they too may contain ingredients, which can aggravate the condition and add to an eczema sufferer's discomfort.

Topical Steroids:

When eczema is under control, normally only emollients are used to manage the condition. However, in flare ups, when the skin becomes inflamed, the use of a steroid cream is widely accepted.

Steroids act by reducing inflammation and are used in most types of eczema.

Topical steroids come in four different strengths, namely, mild, moderately potent, potent and very potent. The strength of steroid cream that a doctor prescribes depends on the age of the patient, the severity of the condition, and the size of the area and part of the body to be treated.

Topical steroids are applied thinly to the affected area, as directed by the prescribing doctor.

One of the disadvantages associated with the use of topical steroids is that they need to be reviewed regularly and moreover, there are concerns regarding side effects related to the use of steroids.

Oral Steroids:

Oral steroids are prescribed to alleviate the symptoms associated with very severe forms of eczema.

As with topical steroids, there are concerns vis-à-vis their associated side effects.

In addition to the above, it is also known to use topical immunomodulators to manage the symptoms associated with eczema.

Psoriasis is an immune-mediated, genetic disease manifesting in the skin and/or joints.

The most common type of psoriasis is plaque psoriasis in which patches of skin, called "lesions", become inflamed and are covered by silvery white scale. Psoriasis can be limited to a few lesions or can involve moderate to large areas of skin. The severity of psoriasis can vary from person to person.

As with eczema, although there are a number of treatments, both topical and systemic, utilised to manage the discomfort caused by the condition and clear psoriasis for periods of time, there is no known cure.

Other forms of psoriasis include guttate, characterised by small dot-like lesions; pustular, characterised by weeping lesions and intense scaling; inverse, characterised by intense inflammation; and erythrodermic, characterised by intense shedding and redness of the skin.

Psoriasis is also linked to other forms of diseases including psoriatic arthritis, which is a specific type of arthritis that has been diagnosed in approximately 23% of people who have psoriasis, that is, according to the Psoriasis Foundation's 2001 benchmark survey. Psoriatic arthritis is similar to rheumatoid arthritis, but not as severe.

One of the symptoms associated with the condition of psoriasis is itching. One of the simplest, ways to control this symptom is by keeping the skin moisturised, because dry skin can induce and aggravate this symptom. To date, treatments to manage the condition of psoriasis include anti-histamines, steroids, topical antiseptics, topical immuno modulators, anti-depressants and aspirin.

As will be appreciated, there is a need for new compositions and products, which are topically administrable and which can alleviate the distress and discomfort caused by eczema and psoriasis and other related skin conditions including those with the symptom of dry itchy skin and/or dry itchy lesions. There is also a need for a new topically administrable product that is less likely to aggravate and/or add to a sufferer's symptoms due to its constituents. Furthermore, there is also a need for a new topically administrable product, which is not steroid based.

It is believed that the topically administrable product of the present application at least addresses some of the problems associated with known products which are used to manage the symptoms associated with eczema and psoriasis and other related skin conditions identified above.

In a first aspect of the present invention, there is provided a product for topical administration which comprises or consists essentially of at least one moisturising agent selected from the group consisting of saccharide isomerate, sodium hyaluronate, phospholipids, biosaccharide gum-1, glycyrrhetinic acid;

at least one repairing agent selected from the group consisting of allantoin, spent grain wax, *argania spinosa* kernel oil, *butyrospermum parkii* (shea butter) extract, and sodium carboxymethyl beta-glucan; and at least one purifying agent selected from the group consisting of 4-terpineol, piroctone olamine; and at least one herbal extract selected from the group consisting of pongamol, *Melia Azadirachta* extract (preferably leaf extract), *Withania Somnifera* extract (preferably root extract), *Aloe Barbadensis* extract (preferably leaf juice).

In a second aspect of the present invention there is provided, a product for topical administration, the product comprising or consisting essentially of herbal extracts or botanical extracts, wherein the herbal extracts include *Melia Azadirachta* extract (preferably *Melia Azadirachta* leaf extract), *Withania Somnifera* extract (preferably *Withania Somnifera* root extract) and *Aloe Barbadensis* extract (preferably *Aloe Barbadensis* leaf juice).

In this second aspect, it is preferable that the product further comprises or further consists essentially of at least one moisturising agent selected from the group consisting of saccharide isomerate, sodium hyaluronate, phospholipids, biosaccharide gum-1, glycyrrhetinic acid; and at least one repairing agent selected from the group consisting of allantoin, spent grain wax, *argania spinosa* kernel oil, *butyrospermum parkii* (shea butter) extract, and sodium carboxymethyl beta-glucan; and at least one purifying agent selected from the group consisting of 4-terpineol, piroctone olamine.

It is believed that the product of the present invention is less likely to aggravate the symptoms associated with eczema and psoriasis, not least because it contains a number of natural herbal or botanical extracts. It is also believed that the product of the present invention is less likely to have side effects, not least because it is not steroid based. It is also believed that the reason why the product of the present invention is less likely to aggravate the symptoms of eczema and psoriasis is because it is not tar or urea based.

Preferred features of the products of the first and second aspect of the present invention are as follows:

Advantageously, the product of the present invention comprises saccharide isomerate, sodium hyaluronate, phospholipids, biosaccharide gum-1, glycyrrhetinic acid; and allantoin, spent grain wax, *argania spinosa* kernel oil, *butyrospermum parkii* (shea butter) extract, and sodium carboxymethyl beta-glucan; and 4-terpineol, piroctone olamine.

Preferably, the *Melia Azadirachta* leaf extract is present in an amount of 0.01%-2.5% w/w, the *Withania Somnifera* root extract is present in an amount of 0.01%-2.5% w/w and the *Aloe Barbadensis* leaf juice is present in an amount of 0.01%-20% w/w. Further preferably, the *Melia Azadirachta* leaf extract is present in an amount of 0.5% w/w, the *Withania Somnifera* root extract is present in an amount of 0.45% w/w and the *Aloe Barbadensis* leaf juice is present in an amount of 0.02% w/w.

Advantageously, the product comprises 0.25%-6.0% w/w of saccharide isomerate, 0.005%-0.5% w/w of sodium hyaluronate, 0.005%-1% w/w of phospholipids, 0.005%-0.8% w/w of biosaccharide gum-1, 0.001%-1% w/w of glycyrrhetinic acid; and 0.1%-5% w/w of allantoin, 0.2%-10% w/w of spent grain wax, 0.1%-20.0% w/w of *argania spinosa* kernel oil, 0.1%-20% w/w of *butyrospermum parkii* (shea butter) extract, and 0.005%-1% w/w of sodium carboxymethyl beta-glucan; and 0.05%-5.0% w/w of 4-terpineol, 0.01%-0.5% w/w of piroctone olamine. More advantageously, the product comprises 2.75% w/w of saccharide isomerate, 0.1% w/w of sodium hyaluronate, 0.07% w/w of phospholipids, 0.055% w/w of biosaccharide gum-1, 0.03% w/w of glycyrrhetinic acid; and 2.0% w/w of allantoin, 2.0% w/w of spent grain wax, 1.75% w/w of *argania spinosa* kernel oil, 1.25% w/w of *butyrospermum parkii* (shea butter) extract, and 0.1% w/w of sodium carboxymethyl beta-glucan; and 1% w/w of 4-terpineol, 0.5% w/w of piroctone olamine.

Preferably, the product of the present invention consists of the ingredients set forth in table 1.

Advantageously, the product of the present invention is in the form of an ointment, a cream or a lotion.

In another aspect of the present invention there is also provided the product of the present invention for use in therapy, in particular, for use in the treatment of eczema or psoriasis or other related skin conditions, including those having the symptom of dry itchy skin and/or dry lesions.

The preferred components of the product of the present invention, together with their sources, are set out below.

Herbal or Botanical Extracts

Pongamol

Pongamol which is commercially known as *Pongamia* extract is extracted from the pongam tree (*Pongamia Pinnata* (L). Pierere). The pongam tree is primarily cultivated for two purposes, namely, for its fragrant Wisteria-like flowers and as a host plant for lac insects.

Well decomposed flowers are used by gardeners as compost for plants requiring nutrients. In some countries, the bark of the pongam tree is used for making strings and ropes. The seeds of the tree contain pongam oil, a bitter, red, brown, thick, non-drying, non-edible oil, 27-36% by weight, which is used for tanning leather, soap and as a liniment to treat scabies, herpes, and rheumatism and as an illuminating oil. The oil has a high content of triglycerides, and its disagreeable taste and odour are due to bitter flavanoid constituents, pongamiin and Karanjin. As will be appreciated, Pongamol has the empirical formula $C_{18}H_{14}O_4$, a molecular weight of 294 and is an off-white cream powder. It is also known to exhibit effective UV absorbing properties.

*Melia Azadirachta* Leaf Extract

*Melia Azadirachta* leaf extract, also know as *Phytessence Margosa*, is extracted from the neem tree, also referred to as the neam tree.

Extracts from the leaves of the margosa tree have been used for a long time in Indian agriculture and medicine. The plant is well known for its insect repellant properties and the therapeutical use of the plant have been laid down in classical texts of Ayurveda. The active agents extracted from the plant are limonoids (salannin) and nimbin (both have anti-inflammatory properties), sulphurus compounds (antibacterial properties) and tannins (act as an astringent).

*Withania Somnifera* Root Extract

*Withania Somnifera* root extract also known as Indian Ginseng or winter cherry grows as a stout shrub that reaches a height of 170 cm. Like the tomato which belongs to the same family, it bears yellow flowers and red fruit, although its fruit is berry like in size and shape.

Fruits, leaves and seeds of this medicinal plant have been traditionally used for the Ayurvedic system as aphrodisiacs, diuretics and for treating memory loss. The active constituents are believed to be anaferine, anahygrine, beta-sisterol, cuscohygrine, iron, pseudotropine, scopoletin, somniferinine, somniferiene, tropanol, withanine, withananine and withanolides A-Y.

*Aloe Barbadensis*

Aloe vera is a member of the tree lilly family, known as *aloe barbadensis*.

There are over 250 species of aloe growing around the world. The most popular species grown today commercially are *aloe barbadensis* miller and *Aloe aborescens.*

The following tabulated list of ingredients, which is not comprehensive, is believed to be the most important aloe vera gel ingredients.

| Category | Typical examples |
| --- | --- |
| Amino acids | Lysine, histidine, arginine, aspartic acid, threonine, serine, hydroxyproline, proline, glycine, alanine, cystine, valine, methionine, isoleucine, leucine, glutamic acid, phenylalanine, tryptophane, tyrosine |
| Enzymes | Amylase, kipase, alkaline phosphatae, bradykinase, carboxypeptidase, catalase, oxidase |
| Minerals | Magnesium, calcium, potassium, sodium, phosphorous, zinc |
| Phytosterols | Beta-Sitosterol, campesterol, lupeol |
| Polysaccharides | Glucomannan, acemannan, pectin, cellulose |
| Vitamins | $B_1$, $B_2$, $B_3$, $B_6$, $B_{12}$, Folic acid |
| Growth factors | Auxins, gibberellins |
| Further active substances | Salicylic acid, malic acid |

Moisturising Agents

As will be appreciated, moisturising is fundamental for the well being of the skin and for the integral preservation of intrinsic mechanical properties including protection, elasticity, subtleness and plasticity.

Water makes up 70% of the skin and 65% of the epidermis. The epidermis is a stratified epithelium; one of the key functions of which is to generate a layer of relative impermeable dead cells known as the stratum corneum.

In order to carry out its role of mechanical, chemical and biological protection, the epidermal barrier must satisfy two conditions; it must be compact, but nevertheless remain subtle and it must desquamate very rapidly in order to permanently retain optimal thickness.

The main stabilising component in this fragile balance lies specifically in the preservation of a critical moisturising level in the corneal layer, which should be between 10 and 15%.

With the above in mind, and as will be appreciated by those in the art, the term, moisturising agent as used herein, is an agent which at least moisturises the skin to the requisite levels. It is also to be appreciated that some of the recited moisturising agents are also soothing agents in that they have proven soothing activity (for example alleviating the discomfort caused by aggressive ingredients such as AHAs (alpha-hydroxy acids), in particular, "in a lactic acid stinging study, Pentavitin® proved to be effective against irritation caused by AHA containing products").

As identified in Table 1, a preferred source of the moisturising agent, saccharide isomerate is Pentavitin®, which corresponds to that of the natural carbohydrate complex found in the stratum corneum. It is highly substantive to skin, and binds itself to keratin thereby creating a moisture reservoir that can only be removed by the natural process of desquamation.

Another moisturising agent for use in the present invention is sodium hyaluronate, which is the sodium salt of hyaluronic acid, a glycosaminoglycan consisting of D-glucuronic acid and N-acetyl-D-glucosamine disaccharide units.

Sodium hyaluronate is extracted from cocks' combs or obtained by fermentation from Streptococci, Lancefield groups A and C. It is preferably produced by methods of manufacture designed to minimise or eliminate infectious agents. When produced by fermentation of gram-positive bacteria, the process must be shown to produce or eliminate pyrogenic or inflammatory components of the cell wall.

As identified in Table 1, a suitable source for the phospholipids and glycyrrhetinic acid is glycyrrhetinic acid phytosome, which is complex of soybean extract and glycyrrhetinic acid, namely, a complex of 18β-Glycyrrhetinic acid and soybean phospholipids.

18β-glycyrrhetinic acid or 3-β hydroxy-11-oxo-olean-12-en-(18-β)-30-oic acid or simply glycyrrhetinic acid is a triterpenic acid obtained from the hydrolysis of glycyrrhizic acid; the main component of liquorice (*Glycyrrhiza glabra* L., family Fabaceae).

It is to be appreciated that the preferred phospholipids is phosphatidylcholine, preferably from soy As identified in Table 1, one suitable source for the moisturising agent biosaccharide gum-1 is a product known as Fucogel®, obtainable from Solabia group (France). In this regard, the polysaccharide biosaccharide gum-1 comprises a repetition of three saccharides, namely, L-fucose, D-galactose and galacturonic acid. The macromolecular structure of this polysaccharide means it has the ability to form a protective, highly moisturising film on the surface of the skin. The resulting human microclimate enhances protection of the skin barrier against dehydration.

Repairing Agents

As will be appreciated, when the skin has been damaged, a set of natural events take place to repair the damage, namely, by regenerating the epidermal or epidermal and dermal tissue, that is, dependent on the severity of the damage. The process of repair is categorised into three overlapping phases, namely, the inflammatory phase, the proliferative phase, and the remodelling phase.

In the inflammatory phase, bacteria and debris are phagocytised and removed and factors are released that cause the migration and division of cells involved in the proliferative phase.

The proliferative phase is generally considered to be characterised by angiogenesis, collagen deposition, granulation tissue formation, epithelialisation, and wound contraction. In angiogenesis, new blood vessels grow from endothelial cells. In fibroplasia and granulation issue formation, fibroblasts grow and form a new, provisional extracellular matrix by excreting collagen and fibronectin. In epithelialisation, epithelial cells crawl across the wound bed to cover it. In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodelling phase, the collagen is remodelled and realigned along the tension lines and cells that are surplus to requirements undergo apoptosis.

In the light of the above, it is to be understood that in the present context, a "repairing agent" is an agent which plays a part in at least one of the phases of the healing process set out above.

One of the preferred repairing agents is allantoin. One suitable source of this non-allergenic botanical extract, namely, allantoin is the comfrey root (*Symphytum officinals* L.). This particular repairing agent promotes wound healing, speeds up cell regeneration and has a skin softening (keratolytic) effect. With specific reference to its wound healing properties, allantoin clears away dead (necrotic) tissue and hastens the growth of new healthy tissue.

Another preferred repairing agent is spent grain wax (*Hordeum Vulgare*). The efficacy of spent grain is due to its unique combination of physiologically invaluable fatty acids, vitamins and phytosterols. In particular, it includes essential fatty acids such as linoleic acid and linolenic acid, which cannot be synthesised by the human body, but are of vital importance to the skin. Keratinocytes need essential fatty acids, like vitamin F for the biosynthesis of membrane lipids in the horny layer. Linoleic acid is crucial for the formation and maintenance of the epidermal permeability barrier. Certain ceramides which are acylated with linoleic acid, strengthen the linkages between lipid bi-layers and the corneocytes. An intact permeability barrier minimises the transepidermal water loss thereby protecting the skin from drying. In addition, linoleic acid is the starting material for the biosynthesis of prostaglandins which, for instance, have important immunoregulatory functions and influence epidermal keratinisation. Two major symptoms associated with essential fatty acid deficiency are epidermal hyperproliferation (scaly skin) and a high level of transepidermal water loss. However, the essential fatty acids are not the only factors playing an important regulatory role in the skin. Fatty acids such as palmitic, myristic, stearic and oleic acids form lipid double layers with ceramide's and cholesterol, which act as a permeability barrier as well.

Vitamins play an important role in the delicate equilibrium of the skin. Locally applied vitamins can reverse the degenerative processes related to skin aging. In particular, vitamin D stimulates cell respiration and fatty acid metabolism, whereas vitamin E ($\alpha$-tocopherol) protects membranes from oxidative and radical damage (lipid peroxidation) and exhibits anti-inflammatory effects. As a membrane stabilising antioxidant, it can inhibit the release of histamine and hydrolitic enzymes from mast cells and lysosymes. Additionally, vitamin E inhibits the synthesis of prostaglandin $E_2$, which is known to take part in inflammatory processes.

Phytosterols like $\beta$-cytosterol have been shown to improve the epidermal barrier and to have anti-pruritic effects.

As identified in table 1, a suitable source of the repairing agents, *argania spinosa* kernel oil and *butyrospermum parkii* (shea butter) extract is Stimu-tex® AS (Pentapharm Ltd), which is the commercial name for a multifunctional active compound that treats sensitive, very dry and itchy skin, protecting it from allergic reactions. This product contains spent grain wax obtained by supercritical $CO_2$ and has a high content of linoleic acid and phytosterols. As touched upon above, Stimu-tex® AS, due to its constituents, can alleviate the symptoms of very dry, itchy and irritated skin, protect the skin from allergic reactions, strengthen the epidermal barrier and exert an anti-inflammatory activity.

Another preferred repairing agent is sodium carboxymethyl beta-glucan, which is a polysaccharide from baker's yeast (*Saccharomyces cervisiae*) and is a $\beta$-(1-3)-linked polyglucose.

Manufacturing Protocol:

One non-limiting example of a process of producing a product in accordance with the present invention will now be described by way of reference to Table 2.

Example 1

The components of phase A were dispersed in water heated to 80° C. with a vacuum-homogenisator. The components are homogenised under vacuum for 45 minutes.

The ingredients of phase B were then added separately at 80° C. and the mixture was homogenised for 10 minutes.

The ingredients of phase C were first dissolved and then added and homogenised under a partial vacuum for 10 minutes.

The ingredients of phase D were added and homogenised for 10 minutes before cooling.

The ingredients of phase E were then added to the mixture at 40° C.

At 37° C., the ingredients of phases F, G, H, I, J were then added separately.

At 28° C., the maximum of air was withdrawn with a vacuum.

The physico-chemical parameters were controlled and the vessel was then emptied.

Trials:

With a view to confirming the efficacy of the product of the present invention it was subjected to the following trial involving 19 participants who all had eczema.

Analysis was conducted on the following trial factors. In particular, for the purpose of analysis, where responses were given on a 9 point scale, a positive response was considered to score=>5.

Figure 1:
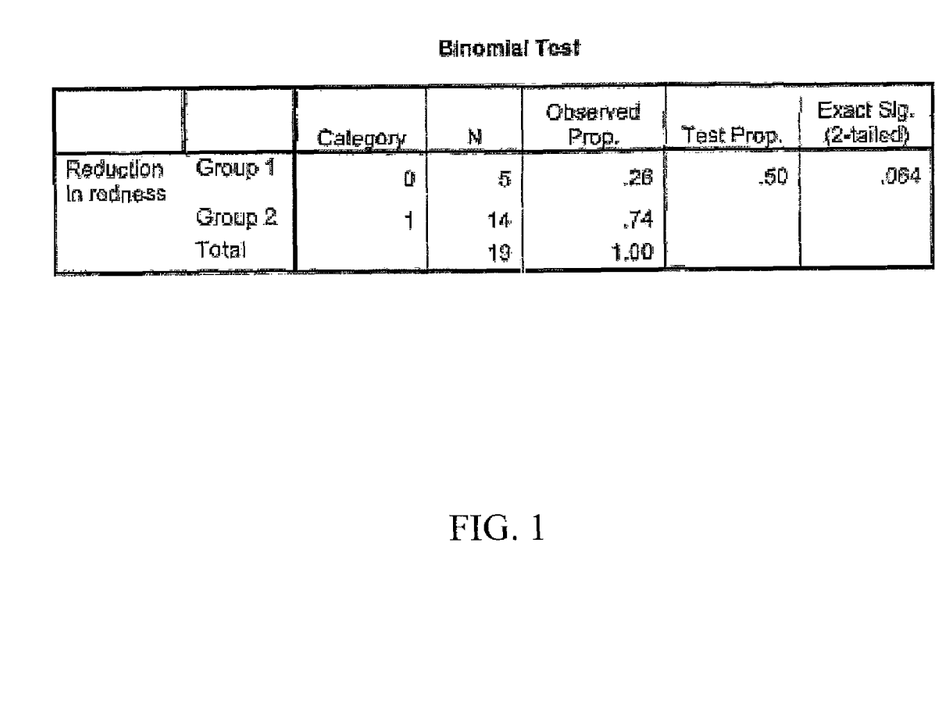
FIGS. 1 and 2 illustrate the test results and charted percentages in redness of an affected area according to an embodiment of the present disclosure.
Figure 2:
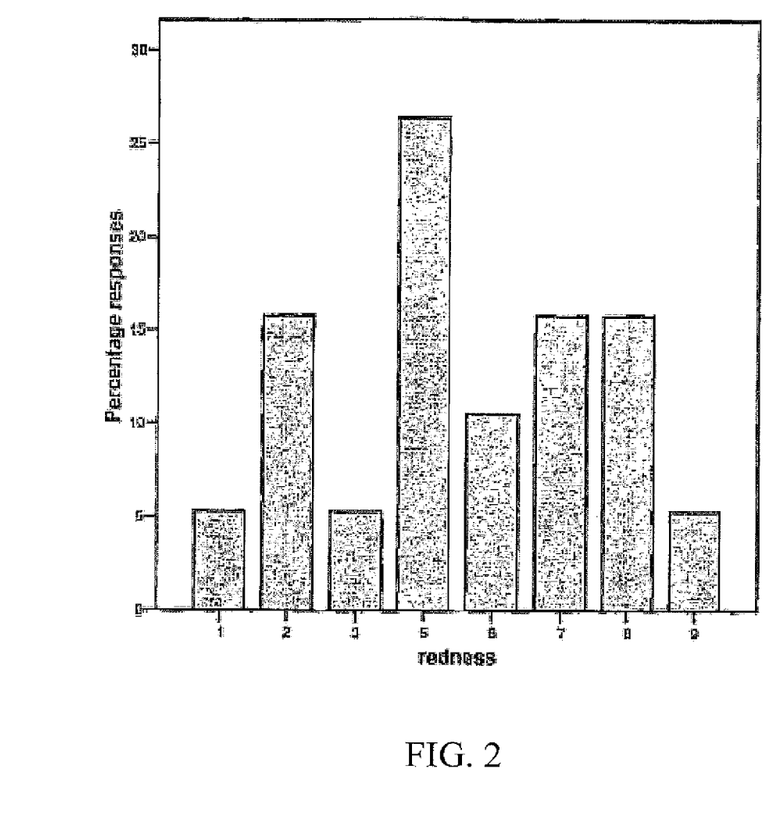

The factors considered were as follows:
1. Reduction in redness of affected area
2. Reduction in discomfort of affected area
3. Reduction in itchiness of affected area
4. Reduction in bleeding of affected area
5. Did the product aid healing of skin?
6. overall rating of product 1. Reduction in Redness of Affected Area From a total of 19 recorded responses, 14 participants (74%) reported that the product reduced redness. Using binomial, a level of significance of p<0.064 was reached. Test results and charted percentages are shown in FIGS. 1 and 2.

2. Reduction in Discomfort of Affected Area

Figure 3:
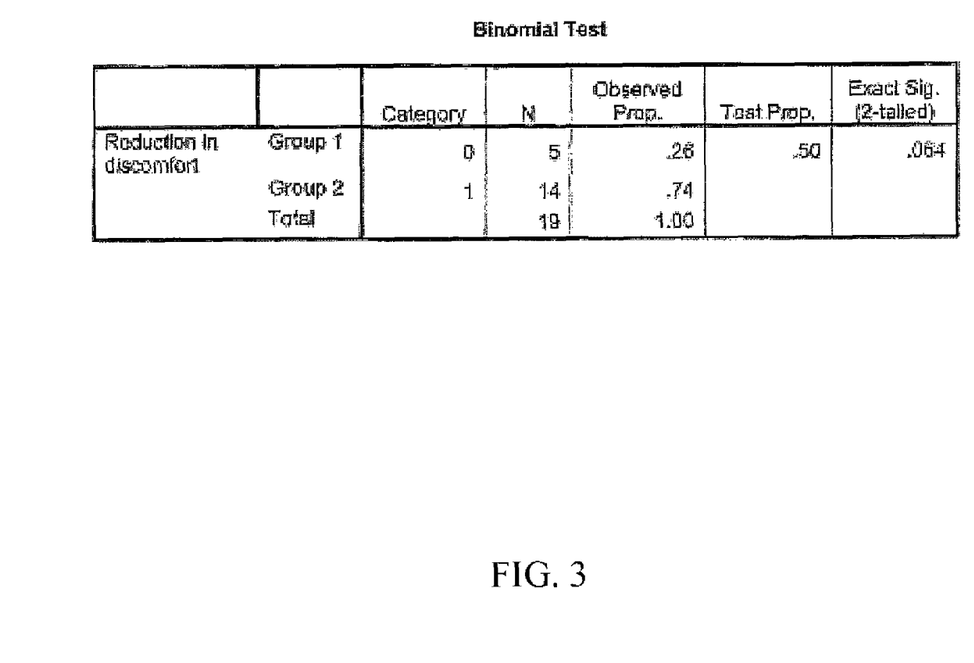
FIGS. 3 and 4 illustrate the test results and charted percentages in discomfort of an affected area according to an embodiment of the present disclosure.
Figure 4:
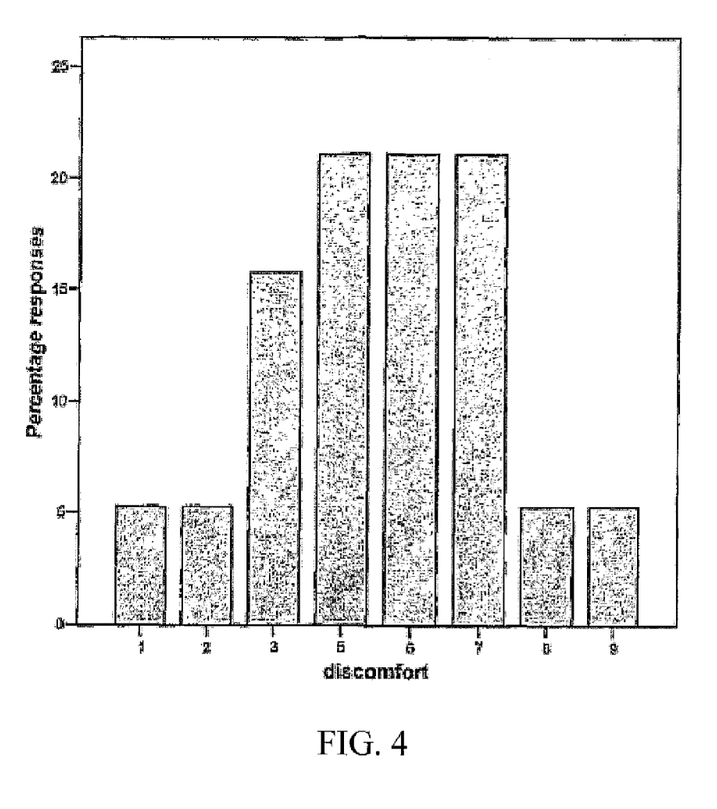

From a total of 19 recorded responses, 14 participants (74%) reported a reduction in discomfort of the affected area. Using binomial, a level of significance of 0.064 was reached. Test results and charted percentages are shown in FIGS. 3 and 4.

3. Reduction in Itchiness of Affected Area

Figure 5:
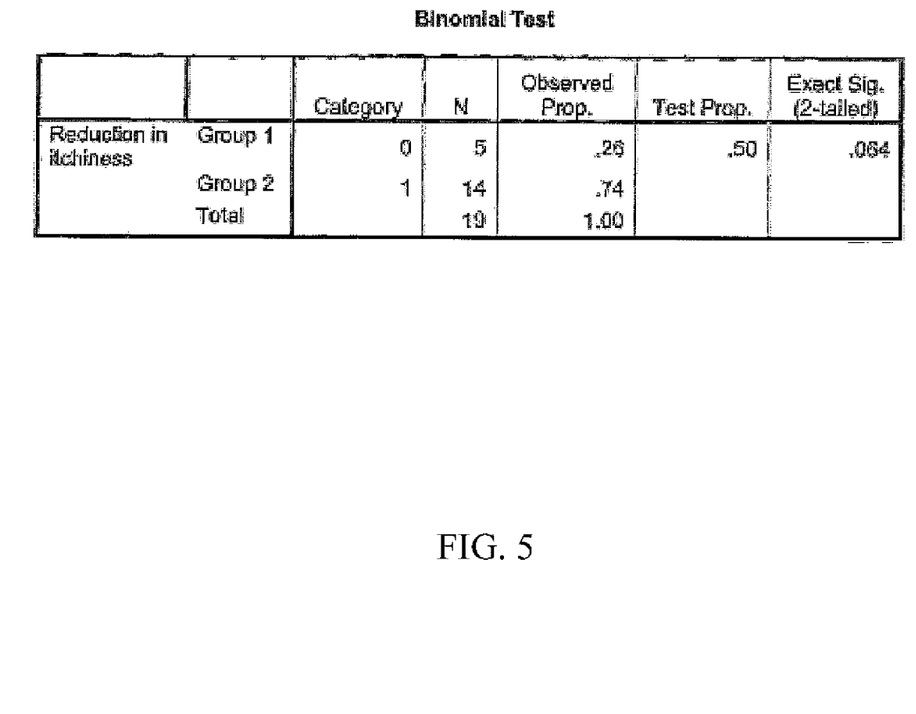
FIGS. 5 and 6 illustrate the test results and charted percentages in itchiness of an affected area according to an embodiment of the present disclosure.
Figure 6:
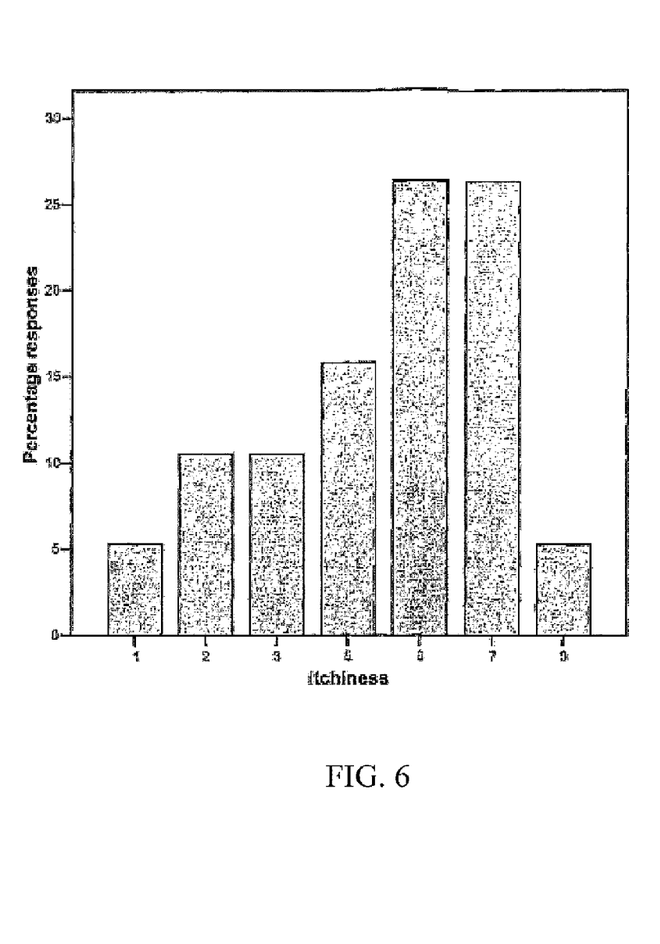

From a total of 19 recorded responses, 14 participants (74%) reported that the product reduced itchiness. Using binomial, a level of significance of 0.064 was reached. Test results and charted percentages are shown in FIGS. 5 and 6.

4. Reduction in Bleeding of Affected Area

Figure 7:
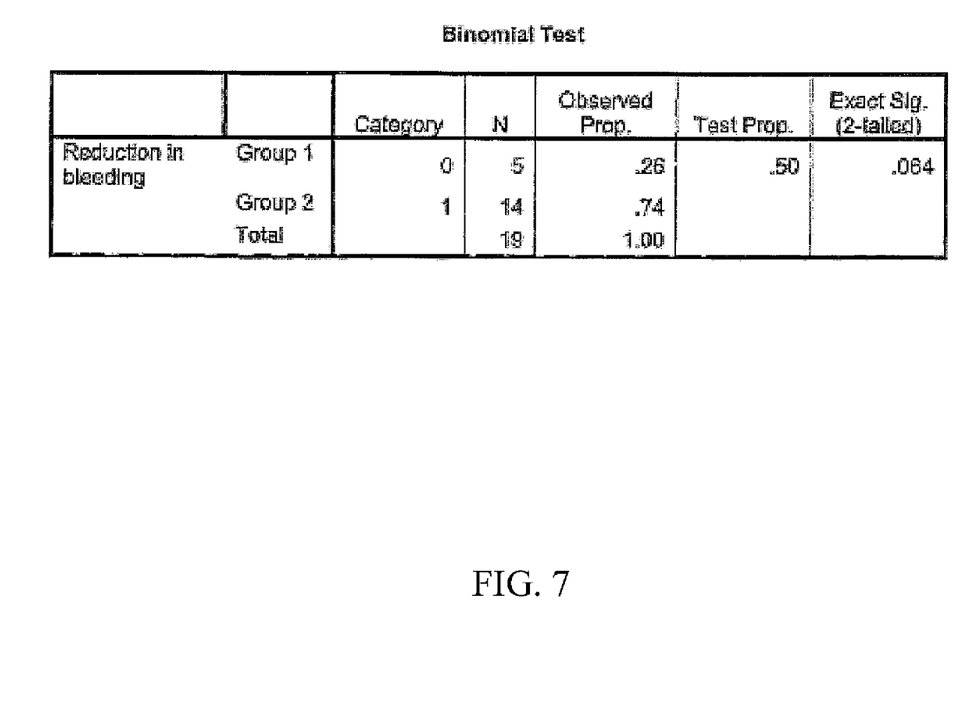
FIGS. 7 and 8 illustrate the test results and charted percentages in bleeding of an affected area according to an embodiment of the present disclosure.
Figure 8:
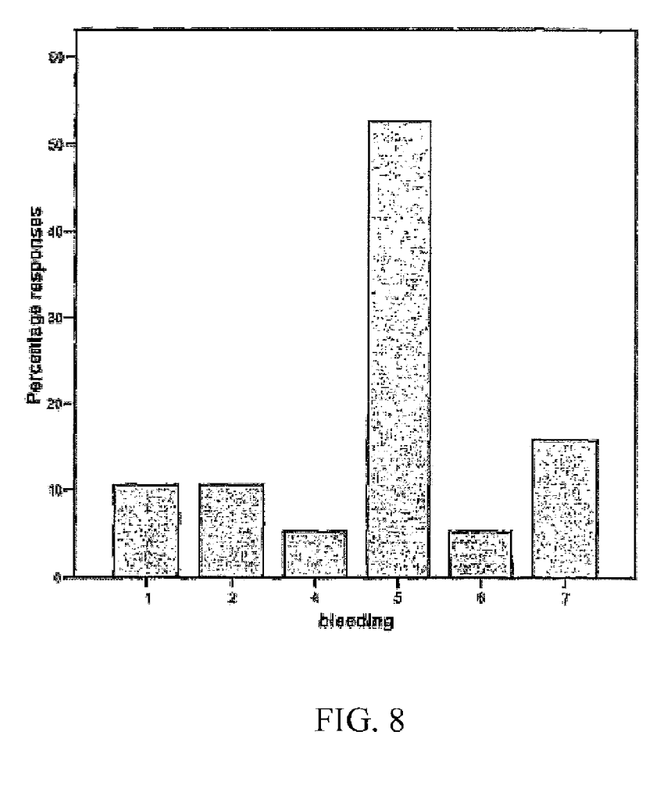

From a total of 19 recorded responses, 14 participants (74%) reported that the product reduced bleeding in the affected area. Using binomial, a level of significance of 0.064 was reached. Test results and charted percentages are shown in FIGS. 7 and 8.

5. Did the Product Aid Healing of Skin?

Figure 9:
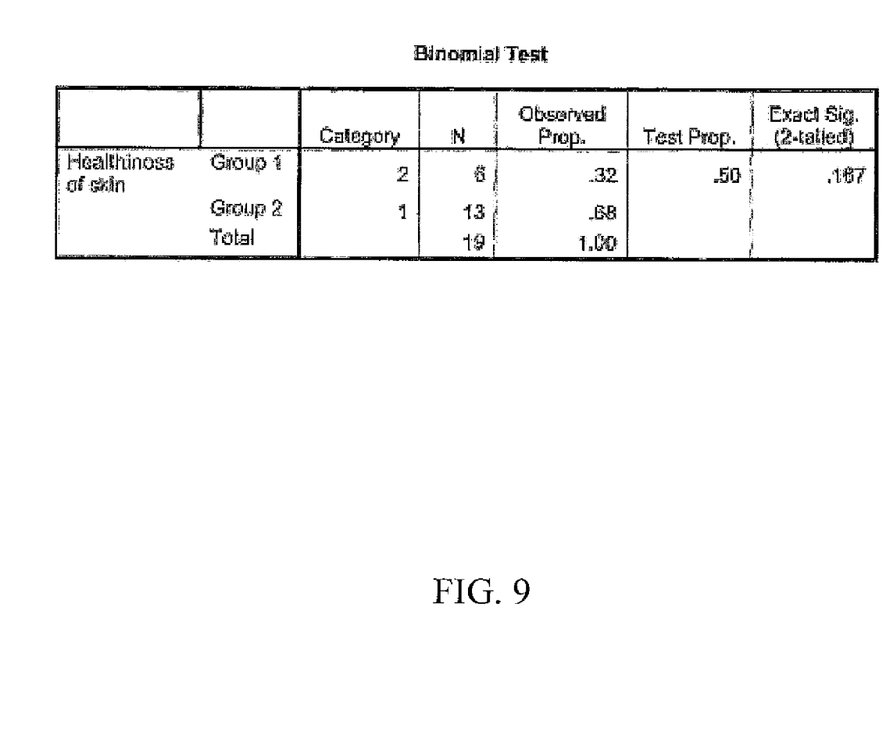
FIGS. 9 and 10 illustrate the test results and charted percentages in healthiness of skin according to an embodiment of the present disclosure.
Figure 10:
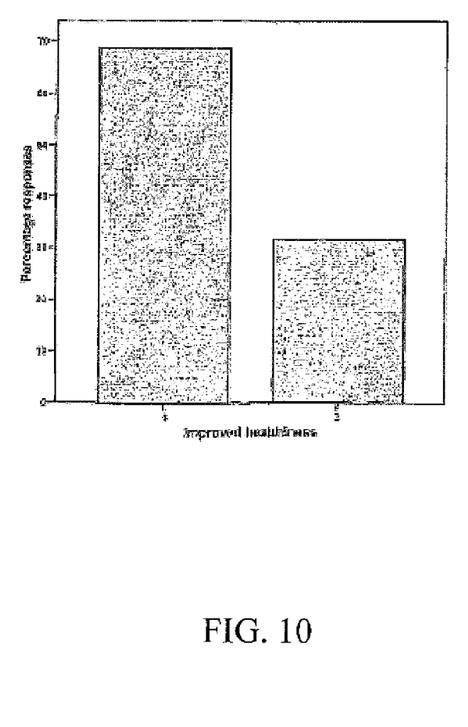

From a total of 19 recorded responses, 13 participants (68%) reported that the product aided healing and a return to healthy looking skin. Using binomial, a level of significance of 0.167 was reached. Test results and charted percentages are shown in FIGS. 9 and 10.

6. Overall Rating of Product

Figure 11:
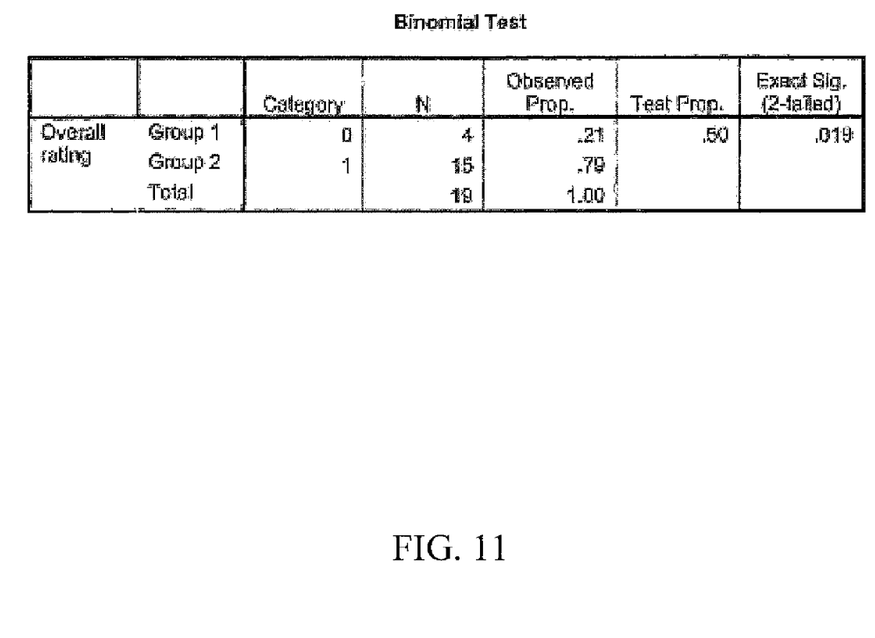
FIGS. 11 and 12 illustrate the test results and charted percentages in overall rating of a product according to an embodiment of the present disclosure.
Figure 12:
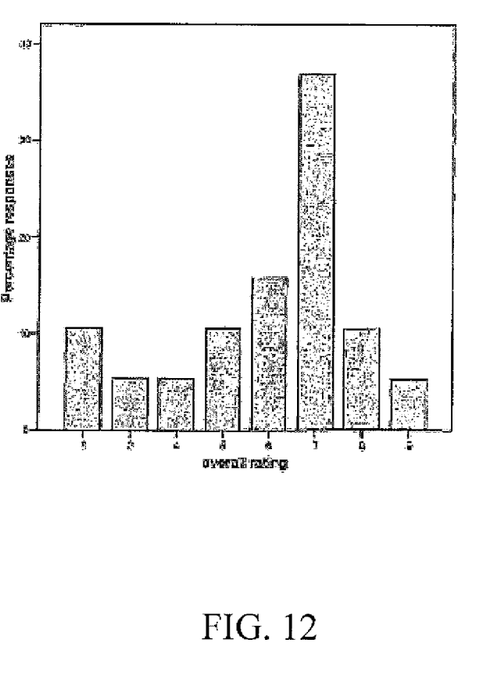

From a total of 19 recorded responses, 15 participants (79%) reported the product to be effective overall. Using binomial, a level of significance of 0.019 was reached ($p<0.02$). Analysis therefore supports the claim that the product is effective. Test results and charted percentages are shown in FIGS. 11 and 12.

As can be seen from the above results, it is clear that the product in accordance with the present invention is able to alleviate and treat the symptoms associated with eczema, psoriasis and like skin conditions.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

TABLE 1

(Source: INCI (International Cosmetic Ingredient Dictionary and Handbook - Eleventh Edition 2006))

| % w/w | % range | INGREDIENTS | Commercial name | Function/CTFA | Function/specific |
|---|---|---|---|---|---|
| QSP 100% | | AQUA/WATER | | Solvent | |
| 13.5000000 | | CAPRYLIC/CAPRIC TRIGLYCERIDE | | Skin-Conditioning Agent | component of oil phase |
| 2.9750000 | | GLYCERIN | | Skin-Conditioning Agent | humectant |
| 2.7500000 | 0.25%-6.0% | SACCHARIDE ISOMERATE | Pentavitin | Skin-Conditioning Agent | Moisturising/soothing |
| 2.5000000 | | SUCROSE STEARATE | | Skin-Conditioning Agent | emulsifying agent |
| 2.3970000 | | ALCOHOL | | Antifoaming Agent | solvent for actives |
| 2.0000000 | 0.1%-5.0% | ALLANTOIN | Allantoin | Skin-Conditioning Agent | Repairing |
| 2.0000000 | 0.2%-10.0% | SPENT GRAIN WAX | Stimu-tex | Skin-Conditioning Agent | Repairing |
| 2.0000000 | | SUCROSE DISTEARATE | | Skin-Conditioning Agent | emulsifying agent |
| 1.7500000 | 0.1%-20.0% | ARGANIA SPINOSA KERNEL OIL | Stimu-tex | Skin-Conditioning Agent | Repairing |
| 1.2500000 | 0.1%-20% | BUTYROSPERMUM PARKII (SHEA BUTTER) EXTRACT | Stimu-tex | Biological Additive | Repairing |
| 1.0500000 | | HEXYLENE GLYCOL | | Solvent | |
| 1.0000000 | 0.05%-5.0% | 4-TERPINEOL | Melaleucol | Fragrance Ingredient | Purifying |
| 1.0000000 | 0.05%-5.0% | PONGAMOL | Pongamia extract | Fragrance Ingredient | Herbal extract |
| 0.5000000 | 0.01%-2.5% | MELIA AZADIRACHTA LEAF EXTRACT | Phytessence Margosa | Skin-Conditioning Agent | Herbal extract |
| 0.4500000 | 0.01%-2.5% | WITHANIA SOMNIFERA ROOT EXTRACT | Withania Somnifera root extract | Skin-Conditioning Agent | Herbal extract |
| 0.0200000 | 0.01%-20.0% | ALOE BARBADENSIS LEAF JUICE | Veragel 200 | Skin-Conditioning Agent | Herbal extract |
| 0.5000000 | | GLYCERYL STEARATE | | Emulsifying Agent | component of oil phase |
| 0.5000000 | 0.01%-0.5% | PIROCTONE OLAMINE | Octopirox | Cosmetic Biocide | Purifying |
| 0.4000000 | | POTASSIUM CETYL PHOSPHATE | | Surfactant | emulsifying agent |
| 0.3000000 | | CARBOMER | | Emulsion Stabilizer | gelling agent |
| 0.2650000 | | CAPRYLYL GLYCOL | | Skin-Conditioning Agent | Preservative |
| 0.2500000 | | PHENOXYETHANOL | | Preservative | |
| 0.1000000 | 0.005%-1.0% | SODIUM CARBOXYMETHYL BETA-GLUCAN | CM Glucan | Binder | Repairing |
| 0.1000000 | 0.005%-0.5% | SODIUM HYALURONATE | | Skin-Conditioning Agent | Moisturising |
| 0.0700000 | 0.005%-1.0% | PHOSPHOLIPIDS | Acide Glycyrrhetinique fitosomes | Skin-Conditioning Agent | Moisturising/soothing |
| 0.0550000 | 0.005%-0.8% | BIOSACCHARIDE GUM-1 | Fucogel | Skin-Conditioning Agent | Moisturising/soothing |
| 0.0300000 | 0.001%-1.0% | GLYCYRRHETINIC ACID | Acide Glycyrrhetinique fitosomes | Skin-Conditioning Agent | Moisturising/soothing |
| 0.0800000 | | DISODIUM EDTA | | Chelating Agent | |
| 0.0705600 | | SODIUM HYDROXIDE | | pH Adjuster | |
| 0.0503500 | | CITRIC ACID | | Chelating Agent/antioxidant | Part of antioxidant complex |
| 0.0220500 | | PEG-8 | | Humectant | Part of antioxidant complex |
| 0.0105000 | | TOCOPHEROL | | Antioxidant | Part of antioxidant complex |
| 0.0017500 | | ASCORBYL PALMITATE | | Antioxidant | Part of antioxidant complex |
| 0.0003500 | | ASCORBIC ACID | | Antioxidant | Part of antioxidant complex |
| 0.0000128 | | DENATONIUM BENZOATE | | Denaturant | In alcohol |

TABLE 2

| Ref. CRB | | Designation CRB | INCI EUROPE + USA + ASIE | Fournisseur |
|---|---|---|---|---|
| | | | Phase A | |
| M06 E010 | QSP 100 | Eau demineralisee sterile | AQUA/WATER | CRB S.A. |
| M09 E180 | 0.080 | Disodium edetate (EDTA) | DISODIUM EDTA | BRENNTAG-SCHWEIZERHALL |
| M12 G520 | 3.500 | Glycerine 85% Ph. Eur II | GLYCERIN AQUA/WATER | CENTONZE EMANUELE |
| M17 D789 | 0.100 | Diocide | CAPRYLYL GLYCOL PHENOXYETHANOL HEXYLENE GLYCOL AQUA/WATER | DIOW PRODUCTS |
| M04 G510 | 0.100 | Acide Glycyrrhetinic Fit. poudre | PHOSPHOLIPIDS GLYCYRRHETINIC ACID | INDENA |
| M07 A075 | 2.000 | Allantoine EP | ALLANTOIN | SLI CHEMICALS |
| M09 A115 | 0.100 | Acide Hyaluronique BT pur (poudre) | SODIUM HYALURONATE | THERAPO LTD |
| M17 C256 | 0.300 | Carbopol Ultrez 10 | CARBOMER | NOVEON |
| | | | Phase B | |
| M07 A555 | 0.400 | Amphisol K | POTASSIUM CETYL PHOSPHATE | GIVAUDAN |
| M17 S030 | 2.000 | Sisterna SP30-C | SUCROSE DISTEARATE | SISTERNA BV |
| M17 S070 | 2.500 | Sisterna SP70-C | SUCROSE STEARATE | SISTERNA BV |
| | | | Phase C | |
| M17 C105 | 9.000 | Capric Caprylic Triglyceride | CAPRYLIC/CAPRIC TRIGLYCERIDE | CENTONZE EMANUELE |
| M07 G580 | 0.500 | Geleol en copeaux | GLYCERYL STEARATE | GATTEFOSSE |
| M17 S770 | 5.000 | Stimu-tex AS code 290-02 | SPENT GRAIN WAX ARGANIA SPINOSA KERNEL OIL BUTYROSPERMUM PARKII (SHEA BUTTER) EXTRACT | PENTAPHARM |
| M17 P670 | 1.000 | Pongamia extract | PONGAMOL | QUEST INTERNATIONAL |
| M17 D789 | 0.100 | Diocide | CAPRYLYL GLYCOL PHENOXYETHANOL HEXYLENE GLYCOL AQUA/WATER | DIOW PRODUCTS |
| M17 O442 | 0.035 | Oxynex K liquid | PEG-8 TOCOPHEROL ASCORBYL PALMITATE ASCORBIC ACID CITRIC ACID | MERCK |
| | | | Phase D | |
| M06 E010 | 1.000 | Eau demineralisee sterile | AQUA/WATER | CRB S.A. |
| M14 H859 | 0.180 | Hydroxyde de Sodium 40% (NaOH) | SODIUM HYDROXIDE AQUA/WATER | BRENNTAG-SCHWEIZERHALL |
| | | | Phase E | |
| M17 D789 | 0.300 | Diocide | CAPRYLYL GLYCOL PHENOXYETHANOL HEXYLENE GLYCOL AQUA/WATER | DIOW PRODUCTS |
| | | | Phase F | |
| M17 P530 | 5.000 | Phytessence Margosa | CAPRYLIC/CAPRIC TRIGLYCERIDE MELIA AZADIRACHTA LEAF EXTRACT | CRODA GmbH |
| | | | Phase G | |
| M06 E010 | 12.000 | Eau demineralisee sterile | AQUA/WATER | CRB S.A. |
| M12 H420 | 1.000 | Hexylene Glycol art. n° 35008 | HEXYLENE GLYCOL | BRENNTAG-SCHWEIZERHALL |
| M17 W100 | 0.450 | Withania Somnifera root ext. | WITHANIA SOMNIFERA ROOT EXTRACT | MMP Inc. |
| M17 V200 | 0.020 | Veragel 200 code TN 003 | ALOE BARBADENSIS LEAF JUICE | TERRY |
| M17 C340 | 0.100 | CM Glucan J | SODIUM CARBOXYMETHYL BETA-GLUCAN | MIBELLE AG |
| | | | Phase H | |
| M17 F015 | 5.000 | Fucogel 1,5 P | BIOSACCHARIDE GUM-1 PHENOXYETHANOL AQUA/WATER | SOLABIA |
| M06 P410 | 5.000 | Pentavitin | SACCHARIDE ISOMERATE CITRIC ACID | PENTAPHARM |

TABLE 2-continued

| Ref. CRB | | Designation CRB | INCI EUROPE + USA + ASIE | Fournisseur |
|---|---|---|---|---|
| | | | AQUA/WATER Phase I | |
| M12 A270 | 2.550 | Alcool Fin F15 | ALCOHOL DENATONIUM BENZOATE AQUA/WATER | BRENNTAG-SCHWEIZERHALL |
| M06 E010 | 0.450 | Eau demineralisee sterile | AQUA/WATER | CRB S.A. |
| M17 O140 | 0.500 | Octopirox | PIROCTONE OLAMINE Phase J | CLARIANT GmbH |
| M17 M240 | 1.000 | Melaleucol | 4-TERPINEOL | PROVITAL France |

The invention claimed is:

1. A therapeutic product adapted for topical administration, the product comprising herbal extracts, wherein the herbal extracts include *Melia Azadirachta* extract present in an amount of 0.5% w/w, *Withania Somnifera* extract present in an amount of 0.45% w/w and *Aloe Barbadensis* juice present in an amount of 0.02% w/w.

2. The product of claim 1 adapted for the treatment of eczema.

3. The product of claim 2 adapted for the treatment of psoriasis.

4. The therapeutic product of claim 1 wherein the product further comprises at least one moisturising agent selected from the group consisting of saccharide isomerate, sodium hyaluronate, phospholipids, biosaccharide gum-1, and glycyrrhetinic acid; at least one repairing agent selected from the group consisting of allantoin, spent grain wax, *argania spinosa* kernel oil, *butyrospermum parkii* (shea butter) extract, and sodium carboxymethyl beta-glucan; and at least one purifying agent selected from the group consisting of 4-terpineol and piroctone olamine.

5. The product of claim 4, wherein the product is formulated as an ointment or a cream.

6. The product of claim 4 adapted for use in therapy.

7. The product of claim 6 adapted for the treatment of eczema.

8. The product of claim 6 adapted for the treatment of psoriasis.

9. The therapeutic product of claim 4, wherein the product comprises saccharide isomerate, sodium hyaluronate, phospholipids, biosaccharide gum-1, glycyrrhetinic acid, allantoin, spent grain wax, *argania spinosa* kernel oil, *butyrospermum parkii* (shea butter) extract, sodium carboxymethyl beta-glucan, 4-terpineol, and piroctone olamine.

10. A method for treating eczema, which comprises administering a therapeutically effective amount of herbal extracts comprising *Melia Azadirachta* leaf extract present in an amount of 0.5% w/w, *Withania Somnifera* root extract present in an amount of 0.45% w/w and *Aloe Barbadensis* leaf juice present in an amount of 0.02% w/w to treat eczema.

11. A method for treating psoriasis, which comprises administering a therapeutically effective amount of herbal extracts comprising *Melia Azadirachta* leaf extract present in an amount of 0.5% w/w, *Withania Somnifera* root extract present in an amount of 0.45% w/w and *Aloe Barbadensis* leaf juice present in an amount of 0.02% w/w to treat psoriasis.

12. A product adapted for topical administration, the product comprising:
at least one moisturising agent selected from the group consisting of saccharide isomerate, sodium hyaluronate, phospholipids, biosaccharide gum-1, and glycyrrhetinic acid;
at least one repairing agent selected from the group consisting of allantoin, spent grain wax, *argania spinosa* kernel oil, *butyrospermum parkii* (shea butter) extract, and sodium carboxymethyl beta-glucan;
at least one purifying agent selected from the group consisting of 4-terpineol and piroctone olamine; and
an herbal mixture comprising *Melia Azadirachta* extract present in an amount of 0.5% w/w, *Withania Somnifera* extract present in an amount of 0.45% w/w, and *Aloe Barbadensis* extract present in an amount of 0.02% w/w.

13. The product of claim 12, wherein the product comprises saccharide isomerate, sodium hyaluronate, phospholipids, biosaccharide gum-1, glycyrrhetinic acid; allantoin, spent grain wax, *argania spinosa* kernel oil, *butyrospermum parkii* (shea butter) extract, sodium carboxymethyl beta-glucan; 4-terpineol, and piroctone olamine.

14. The product of claim 12, wherein the product comprises 0.25%-6% w/w of saccharide isomerate, 0.005%-0.5% w/w of sodium hyaluronate, 0.005%-1% w/w of phospholipids, 0.005%-0.8% w/w of biosaccharide gum-1, 0.001%-1% w/w of glycyrrhetinic acid;
0.1%-5% w/w of allantoin, 0.2%-10% w/w of spent grain wax, 0.1%-20% w/w of *argania spinosa* kernel oil, 0.1%-20% w/w of *butyrospermum parkii* (shea butter) extract, 0.005%-1% w/w of sodium carboxymethyl beta-glucan;
0.05%-5% w/w of 4-terpineol, and 0.01%-0.5% w/w of piroctone olamine.

15. The product of claim 14, wherein the product comprises 2.75% w/w of saccharide isomerate, 0.1% w/w of sodium hyaluronate, 0.07% w/w of phospholipids, 0.055% w/w of biosaccharide gum-1, 0.03% w/w of glycyrrhetinic acid; 2.0% w/w of allantoin, 2.0% w/w of spent grain wax, 1.75% w/w of *argania spinosa* kernel oil, 1.25% w/w of *butyrospermum parkii* (shea butter) extract, 0.1% w/w of sodium carboxymethyl beta-glucan; 1% w/w of 4-terpineol, and 0.5% w/w of piroctone olamine.

16. The product of claim 12, wherein the *Melia Azadirachta* extract comprises *Melia Azadirachta* leaf extract.

17. The product of claim 12, wherein the *Withania Somnifera* extract comprises *Withania Somnifera* root extract.

18. The product of claim 12, wherein the *Aloe Barbadensis* extract comprises *Aloe Barbadensis* leaf juice.

19. A method for treating eczema which comprises administering a therapeutically effective amount of the product of claim 12 for the treatment of eczema.

20. A method for treating psoriasis which comprises administering a therapeutically effective amount of the product of claim 12 for the treatment of psoriasis.

* * * * *